United States Patent
Lowe et al.

(10) Patent No.: US 7,968,349 B2
(45) Date of Patent: Jun. 28, 2011

(54) USE OF HOLOGRAPHIC SENSOR

(75) Inventors: Christopher Robin Lowe, Cambridge (GB); Alexander James Marshall, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 510 days.

(21) Appl. No.: 12/063,726

(22) PCT Filed: Aug. 23, 2006

(86) PCT No.: PCT/GB2006/003156
§ 371 (c)(1),
(2), (4) Date: May 14, 2008

(87) PCT Pub. No.: WO2007/023282
PCT Pub. Date: Mar. 1, 2007

(65) Prior Publication Data
US 2009/0017469 A1    Jan. 15, 2009

(30) Foreign Application Priority Data

Aug. 25, 2005 (GB) .................................. 0517447.9

(51) Int. Cl.
*G01N 33/548* (2006.01)
(52) U.S. Cl. ... 436/528; 422/82.11; 435/7.9; 435/287.2; 435/288.7; 436/164; 436/529; 436/535; 436/805
(58) Field of Classification Search .................. None
See application file for complete search history.

(56) References Cited

U.S. PATENT DOCUMENTS

| 5,141,850 | A | | 8/1992 | Cole et al. |
| 5,352,582 | A | * | 10/1994 | Lichtenwalter et al. .......... 435/6 |
| 5,989,923 | A | | 11/1999 | Lowe et al. |
| 6,319,665 | B1 | | 11/2001 | Zwanziger et al. |
| 6,689,316 | B1 | | 2/2004 | Blyth et al. |
| 2003/0207253 | A1 | | 11/2003 | Kaylor et al. |
| 2004/0002110 | A1 | | 1/2004 | Boga et al. |

FOREIGN PATENT DOCUMENTS

| JP | 08-166388 | 6/1996 |
| WO | WO 92/21977 | 12/1992 |
| WO | WO 03/087789 A | 10/2003 |
| WO | WO 03/087899 A | 10/2003 |
| WO | WO 2004/005537 | 1/2004 |

OTHER PUBLICATIONS

Domschke, A. et al., "Holographic sensors in contact lenses for minimally-invasive glucose measurements," *Sensors*, Proceedings from IEEE Vienna, Austria, Oct. 24-27, 2004, pp. 1320-1323.
Kabilan, S. et al., "Holographic glucose sensors," *Biosensors & Bioelectronics*, Feb. 15, 2005, vol. 20, No. 8, pp. 1602-1610, Elsevier Science Publishers, Barking, GB.

* cited by examiner

*Primary Examiner* — Chris L Chin
(74) *Attorney, Agent, or Firm* — Saliwanchik, Lloyd & Eisenschenk

(57) ABSTRACT

The present invention relates to a process for the detection of an analyte in a sample, comprising a) bringing the sample into contact with a first ligand which binds specifically to the analyte and which is immobilized on a substrate, and b) prior to or subsequent to step (a), bringing the sample into contact with a second ligand which binds specifically to the analyte and which includes a label: wherein the substrate comprises a holographic sensor comprising a support medium having a hologram disposed therein or thereon and the label causes an optical property of the sensor to change by interaction of the sensor with the label or, following the additional step of contacting the substrate with a reagent, by interaction of the sensor with a species produced by reaction of the label with the reagent, thereby indicating the presence of bound analyte.

28 Claims, No Drawings

USE OF HOLOGRAPHIC SENSOR

This application is a National Stage Application of International Application Number PCT/GB2006/003156, filed Aug. 23, 2006; which claims priority to Great Britain Application No. 0517447.9, filed Aug. 25, 2005.

FIELD OF THE INVENTION

The present invention relates to a process for the detection of an analyte in a sample and to a kit for use in such a process.

BACKGROUND OF THE INVENTION

Detection of various analytes can be achieved using assays wherein a sample to be tested is contacted with a substrate which reacts in a detectable manner with the analyte.

Immunoassays are a well known method of analysis based on antibody-antigen interactions which allow for an analyte, which usually acts as the antigen, to be detected. Immunoassays are frequently used in fields such as clinical medicine, forensic medicine, environmental testing, food quality assurance, and drug testing to detect a wide range of immunoreactive analytes in test samples. An example of a common immunoassay is a pregnancy test which uses the binding between an antibody and the hormone human chorionic gonadotropin (hCG) in the blood to indicate pregnancy.

Various different immunoassay methodologies are known such as competitive and non-competitive assays. Although different immunoassay methodologies use different ways to distinguish the presence of an analyte, all immunoassays require the use of a labelled substance to identify the presence of the analyte. The labels are usually identifiable by colour and often comprise dyed latex or a metal particle. Alternatively, the label can include a radioactive compound that is detected through is radioactivity.

Conventional assays are successful but it would advantageous to provide a method of indicating the presence of an analyte without the need for coloured or radioactive labels.

Many conventional assay systems have a safety mechanism which involves, in addition to the process detecting the presence of the analyte, a second parallel process that provides a control so that the user can ensure that the assay has been completed successfully. Having such a safety feature is clearly desirable but results in the use of significantly more reagent than is needed for the actual detection and requires a bulkier construction. It would desirable to provide the control without undertaking a parallel process.

SUMMARY OF THE INVENTION

According to a first aspect, the present invention provides a process for the detection of an analyte in a sample, comprising
  a) bringing the sample into contact with a first ligand which binds specifically to the analyte and which is immobilised on a substrate; and
  b) prior to or subsequent to step (a), bringing the sample into contact with a second ligand which binds specifically to the analyte and which includes a label;
wherein the substrate comprises a holographic sensor comprising a support medium having a hologram disposed therein or thereon and the label causes an optical property of the sensor to change by interaction of the sensor with the label or, following the additional step of contacting the substrate with a reagent, by interaction of the sensor with a species produced by reaction of the label with the reagent, thereby indicating the presence of bound analyte.

According to a second aspect, the invention provides a kit comprising, packaged separately or in combination
  a substrate having a first ligand immobilised thereon and comprising a holographic sensor which comprises a support medium having a hologram disposed therein or thereon; and
  a second ligand which includes a label.

The holographic sensors used in the present invention are highly sensitive to a particular analyte and can give rapid and very accurate results.

Furthermore, the sensors can be designed so that a change in a further optical property of the sensor occurs when the sample and/or the second ligand are brought into contact with the substrate. Hence, the process can be designed to detect whether or not the assay has been successfully, obviating the need for a parallel process thereby providing a safety feature in an efficient way.

DETAILED DESCRIPTION OF THE INVENTION

In traditional assays, the label is directly delectable. In contrast, in the present invention the label is detectable via the effect it has on a holographic sensor. In particular the label or a product resulting from the reaction between the label and a reagent interacts with the sensor to show the results of the process, ie. to indicate the presence of an analyte. Holographic sensors comprise a support medium having a hologram disposed therein or thereon. The support medium is preferably a hydrogel matrix. The sensor of the present invention is located on a substrate wherein the substrate also has a first ligand immobilised thereon. The ligand is attached on or close to the support matrix.

Holographic sensors undergo interactions with various molecules which can be chemical or biological species. The interaction causes variation of a physical property of the support medium and such variation causes a change in the optical characteristics of the holographic sensor which is remotely detectable.

The physical property of the support medium which changes may be its charge density, volume, shape, density, viscosity, strength, hardness, charge, hydrophobicity, swellability, integrity, cross-link density or any other physical property. Variation of the or each physical property, in turn, causes a variation of an optical characteristic such as polarisability, reflectance, refractance or absorbence of the hologram. Preferably, the change in optical characteristics of the hologram is a change in the wavelength which can be observed as a visible change in the colour.

Holographic sensors can be prepared using the diffraction of light by passing a single diverged laser beam through a specially designed analyte-responsive hydrogel coated on a transparent substrate (plastic or glass) backed by a mirror. Interference between the incident and reflected laser beams, followed by photographic development and fixing, creates holographic fringes lying in planes approximately parallel with the hydrogel surface. Under ordinary white light illumination, constructive interference between partial reflections from each fringe plane gives rise to a characteristic spectral peak with a wavelength governed by the Bragg equation.

Changes in the spacing of the fringes or the average refractive index will generate observable changes in the wavelength (colour) of the reflection hologram that are discernable by eye or spectrophotometrically. If the polymer matrix swells in response to interaction with a biological species, the spacing between the fringes increases, causing a longer wavelength of light to be reflected. Conversely, if the polymer matrix contracts in response to the interaction the light that is reflected shifts from longer to shorter wavelengths.

The holographic image is preferably an object or gives a 2- or 3-dimensional effect. The hologram may be visible is only visible under magnification or may be viewable under white light, UV light, infra-red radiation or under specific temperature, magnetism or pressure conditions. The holographic sensor may further comprise means for producing an interference effect when illuminated with laser light, preferably wherein the means comprises a depolarising layer.

Holographic sensors which are suitable for use in the present invention and their manufacture are known, for example, from WO 03/087899 or WO95/26499, the contents of which are incorporated herein by reference.

The process of the invention involves bringing the sample into contact with both a first ligand and a second ligand where both of the ligands bind specifically to the analyte. The sample may be contacted with the second ligand before or after it is contacted with the first ligand. The first ligand is immobilised on a substrate with which the sample is contacted. Hence, when the process has taken place, if the analyte is present it will be bound to both ligands and will, as a result of the first ligand, be immobilised on the substrate. This type of assay is commonly known as a "sandwich assay" because of the sandwich formed of the analyte between the two ligands.

Sandwich assays are known, for example from WO92/21977, U.S. Pat. Nos. 6,319,665 and 5,141,850 the contents of which are incorporated herein by reference. The apparatus and precise method used for carrying out steps a) and b) of the method of the invention are not critical to the invention and any conventional apparatus and methods may be used, such as those described in WO92/21977, U.S. Pat. Nos. 6,319,665 and 5,141,850.

The present invention can be used with any analyte or ligands provided that the ligands bind specifically to the analyte. For example, the analyte may be DNA with DNA bonding ligands. However, the invention is preferably an immunoassay wherein the specific bonding between the analyte and ligands is a result of antibody/antigen interactions. Preferably the first and/or the second ligand is an antibody. The analyte usually contains antigenetic material and can be a biological molecule, for example, an enzyme, a protein, a bacteria or a virus. The invention can be used to detect haemoglobin.

The second ligand includes a label which provides interaction with the holographic sensor thereby changing a property of the sensor. The immobilisation of the label on the substrate indicates that a "sandwich" has been formed and hence indicates the presence of the analyte.

As is conventional, after the first and second ligands have been contacted with the sample, the substrate is washed to remove any unreacted second ligand thereby leaving only the labels that have become immobilised on the substrate as a result of the presence of the analyte. A further step is carried out to allow the label, or a product thereof to interact with the sensor. This usually involves contacting the substrate with a reagent which reacts with the label. The label or part of the label may be may be cleaved from the ligand so that it can interact with the sensor. Alternatively, the reagent may interact with the label to product a species which can interact with the sensor.

In a preferred embodiment, the label is an enzyme. Enzymes are advantageously employed in the invention as labels as they can provide amplification of the response. In this case, a reagent is added which reacts with the enzyme to produce a species that interacts with the sensor to give a detectable change in the optical characteristics.

When the label is an enzyme, the process relies on holographic transducers that are capable of quantifying the rate of specific enzymatic reactions. By labelling an appropriate component (the second ligand) with a particular enzyme, the quantity of that component can be determined by monitoring the optical properties of an associated holographic sensor upon addition of a reagent that reacts specifically with the enzyme.

For example, an antibody or antigen labelled with penicillinase as the label could be quantified with a pH-sensitive hologram upon addition of the reagent penicillin which is converted to penicillic acid on contact with the penicillinase and hence gives a change in the pH sensitive holographic sensor. Alternatively, the quantity of a urease-labelled antibody or antigen could be determined with a sensor hologram containing appropriate crown ethers upon addition of the reagent urea.

As many different enzyme/sensor hologram combinations are possible, this approach provides a flexible and generic immunoassay format which can be utilized with almost any antibody/antigen system. All classes of enzyme are suitable including redox, kinases, phosphatases, proteases etc and these can be configured as part of a coenzymatic cycling system or an amplification cascade. Furthermore, other catalytic entities can be deployed such as synzymes, abzymes, ribozymes and deoxyribozymes, as well as other organic and inorganic catalytic systems.

As mentioned above, it is desirable for a change in a further optical property of the sensor to occur when the sample and/or the second ligand are brought into contact with the substrate.

This can be achieved by having different interaction sites on the sensor. As well as the sites that interact with the label or a species associated with the label, the sensor has sites that interact with markers in the sample and/or in the second ligand carrier. When the sample and/or the second ligand carrier contact the substrate, the markers interact with the sensor to product a characteristic change in the optical characteristics.

The characteristic change in optical properties shows that the sample and/or the second ligand carrier have contacted the substrate hence showing that the assay has been carried out successfully. This gives the user confidence that the results obtained are reliable and is an important safety feature.

A change in the optical properties of the sensor can be observed with the naked eye or with an optical reader. A optical reader can be a spectrophotometer which has the ability to measure hundreds of spectral bands with a resolution of 1 nm. In contrast, the human eye relies on any three spectral bands, blue, green and red corresponding to the three visual pigments. A spectrophotometer can detect very small changes in the optical characteristics which gives a very sensitive result.

The present invention also relates to a kit for use in the method of the invention comprising a substrate having a first ligand immobilised thereon and comprising a holographic sensor which comprises a support medium having a hologram disposed therein or thereon and a second ligand which includes a label.

The invention may be used in many different applications. In the medical field the invention can be used to detect a wide variety of biological or chemical species which are indicative of a certain medical conditions.

The invention is also useful in the field of security as the substrate can be part of an article allowing for the article to be tested to confirm the authenticity.

The substrate including the sensor can be on or on an article that is included in the kit of the present invention which includes a transaction card, banknote, passport, identification card, smart card, driving licence, share certificate, bond, cheque, cheque card, tax banderole, gift voucher, postage stamp, rail or air ticket, telephone card, lottery card, event ticket, credit or debit card, business card, or an item used in consumer, brand or product protection for the purpose of distinguishing genuine products from counterfeit products or identifying stolen products.

Alternatively, the article may be an industrial or handicraft item comprising a decorative element, selected from items of jewellery, items of clothing (including footwear), fabric, furniture, toys, gifts, household items (including crockery and glassware), architecture (including glass, tile, paint, metals, bricks, ceramics, wood, plastics and other internal and external installations), art (including pictures, sculpture, pottery and light installations), stationery (including greetings cards, letterheads and promotional material) and sporting goods.

The article can be a product or device for use in agricultural studies, environmental studies, human or veterinary prognostics, theranostics, diagnostics, therapy or chemical analysis, for example a test strip, chip, cartridge, swab, tube, pipette, contact lens, sub-conjuctival implant, sub-dermal implant, breathalyser, catheter or a fluid sampling or analysis device.

The article can be an item of intelligent packaging. "Intelligent packaging" refers to a system that comprises part of, or an attachment to, a container, wrapper or enclosure, to monitor, indicate or test product information or quality or environmental conditions that will affect product quality, shelf life or safety and typical applications, such as indicators showing time-temperature, freshness, moisture, alcohol, gas, physical damage and the like.

In the kit of the present invention, the substrate may be in or on a transferable holographic film such as a hot stamping tape. A kit may be capable of generating data from the sensor.

EXAMPLE

A first antibody is immobilised on or near a pH sensitive holographic sensor. The support matrix of the sensor comprises a polyHEMA co-polymer with 5% EDMA cross-linker and 6% methacrylic acid.

A sample containing haemoglobin is washed over the immobilised antibodies. The whole haemoglobin that is present in the sample (but not haem or broken down part parts of haem) binds to the first antibody.

A second antibody, labelled with the protein penicillinase, is washed over the surface of the system.

The second antibody binds to the immobilised haemoglobin (which is bound to the first antibody) to form a sandwich.

A solution containing penicillin is then washed over the surface of the system and the protein penicillinase which forms the label on the second antibody converts the penicillin to penicilloic acid.

The formation of penicilloic acid results in a pH change which is registered by a change in the diffraction signal of the hologram. The diffraction signal of the holograms shifts from the infra red (invisible) to the red (visible) as penicilloic acid is produced and the pH drops (becomes more acidic).

The invention claimed is:

1. A process for the detection of an analyte in a sample, comprising
   a) bringing the sample into contact with a first ligand which binds specifically to the analyte and which is immobilized on a substrate; and
   b) prior to or subsequent to step (a), bringing the sample into contact with a second ligand which binds specifically to the analyte and which includes a label;
   wherein the substrate comprises a holographic sensor comprising a support medium having a hologram disposed therein or thereon and the label causes an optical property of the sensor to change by interaction of the sensor with the label or, following the additional step of contacting the substrate with a reagent, by interaction of the sensor with a species produced by reaction of the label with the reagent, thereby indicating the presence of bound analyte,
   wherein the process further corn rises the ste of: c) washing the sensor to remove unreacted labeled second ligand,
   wherein the support medium is a hydrogel matrix, and
   wherein the first ligand is in the hydrogel matrix.

2. The process according to claim 1, wherein a change in a further optical property of the sensor occurs when the sample and/or the second ligand are brought into contact with the substrate.

3. The process according to claim 1, wherein the first ligand and/or the second ligand is an antibody.

4. The process according to claim 1, wherein the analyte is antigenetic material.

5. The process according to claim 4, wherein the analyte is haemoglobin.

6. The process according to claim 1, wherein the label is an organic or inorganic catalytic system.

7. The process according to claim 1, wherein the label is selected from the group consisting of enzymes, synzymes, abzymes, ribozymes, and deoxyribozymes.

8. The process according to claim 7, wherein the label is an enzyme.

9. The process according to claim 6, additionally comprising the step of contacting the substrate with a reagent which reacts with the catalytic system to produce a species which interacts with the sensor.

10. The process according to claim 9, wherein the species produced by reaction of the reagent with the catalytic system has a different pH than the reagent.

11. The process according to claim 1, wherein the hologram is generated by the diffraction of light.

12. The process according to claim 1, wherein the hologram is only visible under magnification.

13. The process according to claim 1, wherein the holographic image is of an object or is a 2- or 3-dimensional effect.

14. The process according to claim 1, wherein the sensor further comprises means for producing an interference effect when illuminated with laser light.

15. The process according to claim 14, wherein the means comprises a depolarising layer.

16. The process according to claim 1, wherein the hologram is viewable under white light, UV light or infra-red radiation.

17. The process according to claim 1, wherein the hologram is viewable under specific temperature, magnetism or pressure conditions.

18. The process according to claim 1, wherein the reaction between the label and the sensor is a chemical reaction.

19. A kit comprising, packaged separately or in combination,
   a substrate having a first ligand immobilized thereon and comprising a holographic sensor which comprises a support medium having a hologram disposed therein or thereon; and a second ligand which includes a label;
wherein the support medium is a hydrogel matrix, and
wherein the first ligand is in the hydrogel matrix.

20. The kit according to claim 19, wherein the substrate is part of an article.

21. The kit according to claim 20, wherein the article is a transaction card, banknote, passport, identification card, smart card, driving licence, share certificate, bond, cheque, cheque card, tax banderole, gift voucher, postage stamp, rail or air ticket, telephone card, lottery card, event ticket, credit or debit card, business card, or an item used in consumer, brand or product protection for the purpose of distinguishing genuine products from counterfeit products or identifying stolen products.

22. The kit according to claim 20, wherein the article is an item of intelligent packaging.

23. The kit according to claim 20, wherein the article is a industrial or handicraft item comprising a decorative element, selected from items of jewellery, items of clothing, fabric, furniture, toys, gifts, household items, architecture, art, stationery and sporting goods.

24. The kit according to claim 20 wherein the article is a product or device for use in agricultural studies, environmental studies, human or veterinary prognostics, theranostics, diagnostics, therapy or chemical analysis.

25. The kit according to claim 24 wherein the article is a test strip, chip, cartridge, swab, tube, pipette, contact lens, sub-conjuctival implant, sub-dermal implant, breathalyser, catheter or a fluid sampling or analysis device.

26. The kit according to claim 20, wherein the substrate is in or on a transferable holographic film.

27. The kit according to claim 26, wherein the film is present on a hot stamping tape.

28. The kit according to claim 19, which is capable of generating data from the sensor.

* * * * *

UNITED STATES PATENT AND TRADEMARK OFFICE
CERTIFICATE OF CORRECTION

| | | |
|---|---|---|
| PATENT NO. | : 7,968,349 B2 | Page 1 of 1 |
| APPLICATION NO. | : 12/063726 | |
| DATED | : June 28, 2011 | |
| INVENTOR(S) | : Christopher Robin Lowe and Alexander James Marshall | |

It is certified that error appears in the above-identified patent and that said Letters Patent is hereby corrected as shown below:

Column 6,
Line 13, "corn rises the ste of" should read --comprises the step of--

Signed and Sealed this
Fourth Day of October, 2011

David J. Kappos
*Director of the United States Patent and Trademark Office*